United States Patent
Jansen et al.

(10) Patent No.: US 7,877,131 B2
(45) Date of Patent: Jan. 25, 2011

(54) METHOD FOR PROVIDING PELVIC ORIENTATION INFORMATION IN COMPUTER-ASSISTED SURGERY

(75) Inventors: Herbert André Jansen, Montréal (CA); Isabelle Fontaine, Montréal (CA); Daniel Odermatt, Montréal (CA)

(73) Assignee: Orthosoft Inc., Montreal (CA)

( * ) Notice: Subject to any disclaimer, the term of this patent is extended or adjusted under 35 U.S.C. 154(b) by 1447 days.

(21) Appl. No.: 10/530,192

(22) PCT Filed: Oct. 6, 2003

(86) PCT No.: PCT/CA03/01542

§ 371 (c)(1), (2), (4) Date: Dec. 8, 2005

(87) PCT Pub. No.: WO2004/030559

PCT Pub. Date: Apr. 15, 2004

(65) Prior Publication Data

US 2006/0100504 A1 May 11, 2006

Related U.S. Application Data

(60) Provisional application No. 60/415,809, filed on Oct. 4, 2002, provisional application No. 60/465,805, filed on Apr. 28, 2003.

(51) Int. Cl.
*A61B 6/03* (2006.01)

(52) U.S. Cl. .................. 600/424; 600/426; 600/407

(58) Field of Classification Search ................. None
See application file for complete search history.

(56) References Cited

U.S. PATENT DOCUMENTS

| 2,703,080 | A  | * | 3/1955 | Sanders ........................ 601/24 |
| 6,405,072 | B1 | * | 6/2002 | Cosman ....................... 600/426 |
| 6,514,219 | B1 |   | 2/2003 | Guimond et al. |

(Continued)

FOREIGN PATENT DOCUMENTS

DE 200 16 635 U 2/2001

(Continued)

OTHER PUBLICATIONS

U.S. Appl. No. 60/415,809, filed Oct. 4, 2002, Jansen et al.

*Primary Examiner*—Unsu Jung
*Assistant Examiner*—Lawrence N Laryea
(74) *Attorney, Agent, or Firm*—Ogilvy Renault LLP

(57) ABSTRACT

A computer-assisted surgery system for guiding an operator in altering a pelvis. A sensing apparatus is provided for tracking a reference tool and a bone altering tool. A position calculator calculates a position and orientation of a pelvic frame of reference as a function of the tracking of the reference tool, and for calculating a position and orientation of the bone altering tool with respect to the frame of reference. A source of posture data and a posture data correction calculator are provided and are operative to provide a display of information allowing an operator to take into consideration the posture data from the source of posture data when altering the pelvis. A display unit is connected to the position calculator and to the posture data correction calculator for displaying the display of information and the bone altering tool with respect to the pelvic frame of reference.

18 Claims, 3 Drawing Sheets

U.S. PATENT DOCUMENTS

| | | | |
|---|---|---|---|
| 7,302,288 B1 * | 11/2007 | Schellenberg | 600/427 |
| 2002/0077540 A1 * | 6/2002 | Kienzle, III | 600/424 |
| 2002/0107522 A1 | 8/2002 | Picard et al. | |
| 2002/0198451 A1 * | 12/2002 | Carson | 600/424 |
| 2003/0153829 A1 * | 8/2003 | Sarin et al. | 600/426 |
| 2003/0176783 A1 * | 9/2003 | Hu | 600/429 |
| 2004/0087852 A1 * | 5/2004 | Chen et al. | 600/407 |
| 2004/0111024 A1 * | 6/2004 | Zheng et al. | 600/426 |
| 2004/0117026 A1 * | 6/2004 | Tuma et al. | 623/18.11 |
| 2004/0181149 A1 * | 9/2004 | Langlotz et al. | 600/431 |
| 2005/0065617 A1 * | 3/2005 | Moctezuma de la Barrera et al. | 623/908 |
| 2005/0203384 A1 * | 9/2005 | Sati et al. | 600/426 |

FOREIGN PATENT DOCUMENTS

| | | |
|---|---|---|
| WO | WO 02/062248 A | 8/2002 |
| WO | WO 02/062250 A | 8/2002 |
| WO | WO03/096920 | 11/2003 |

\* cited by examiner

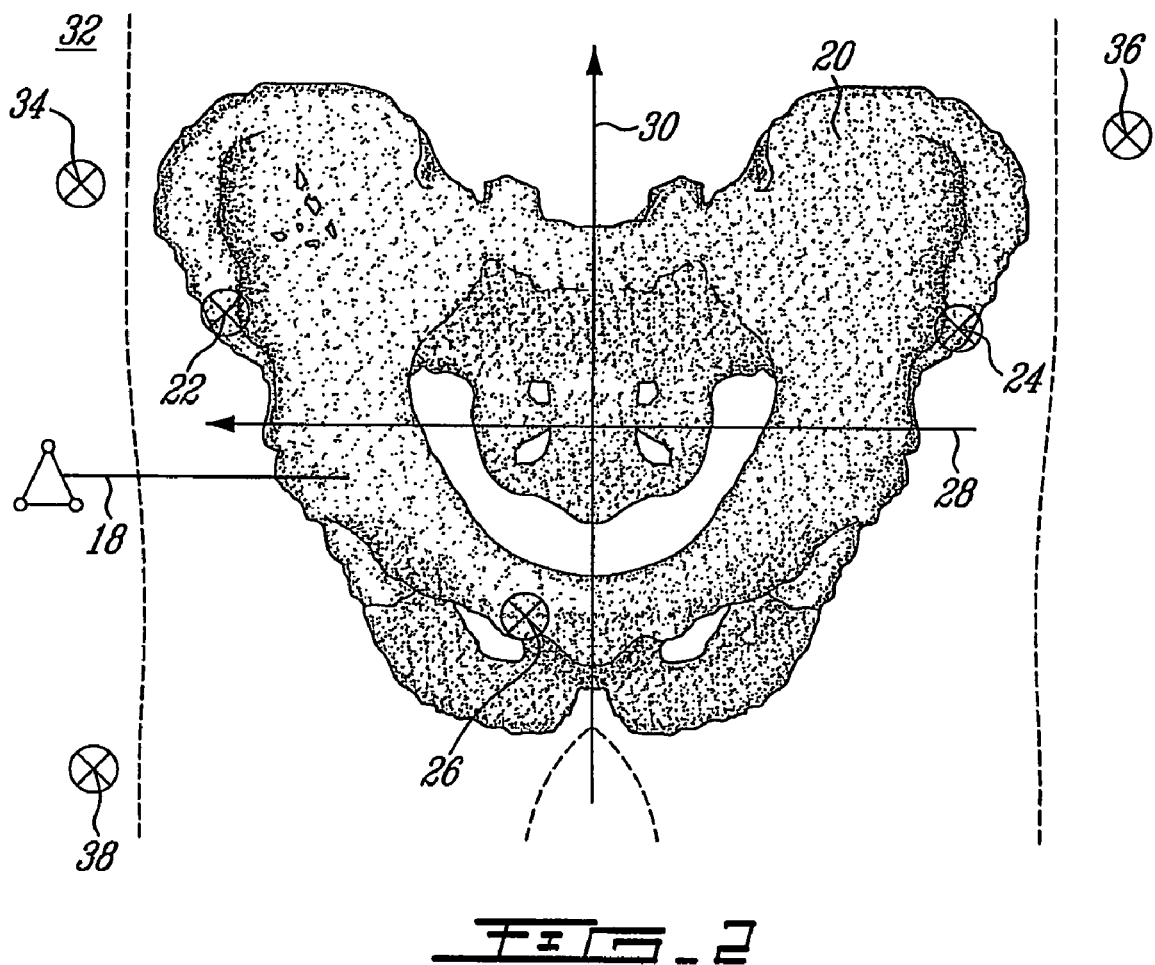
FIG_2

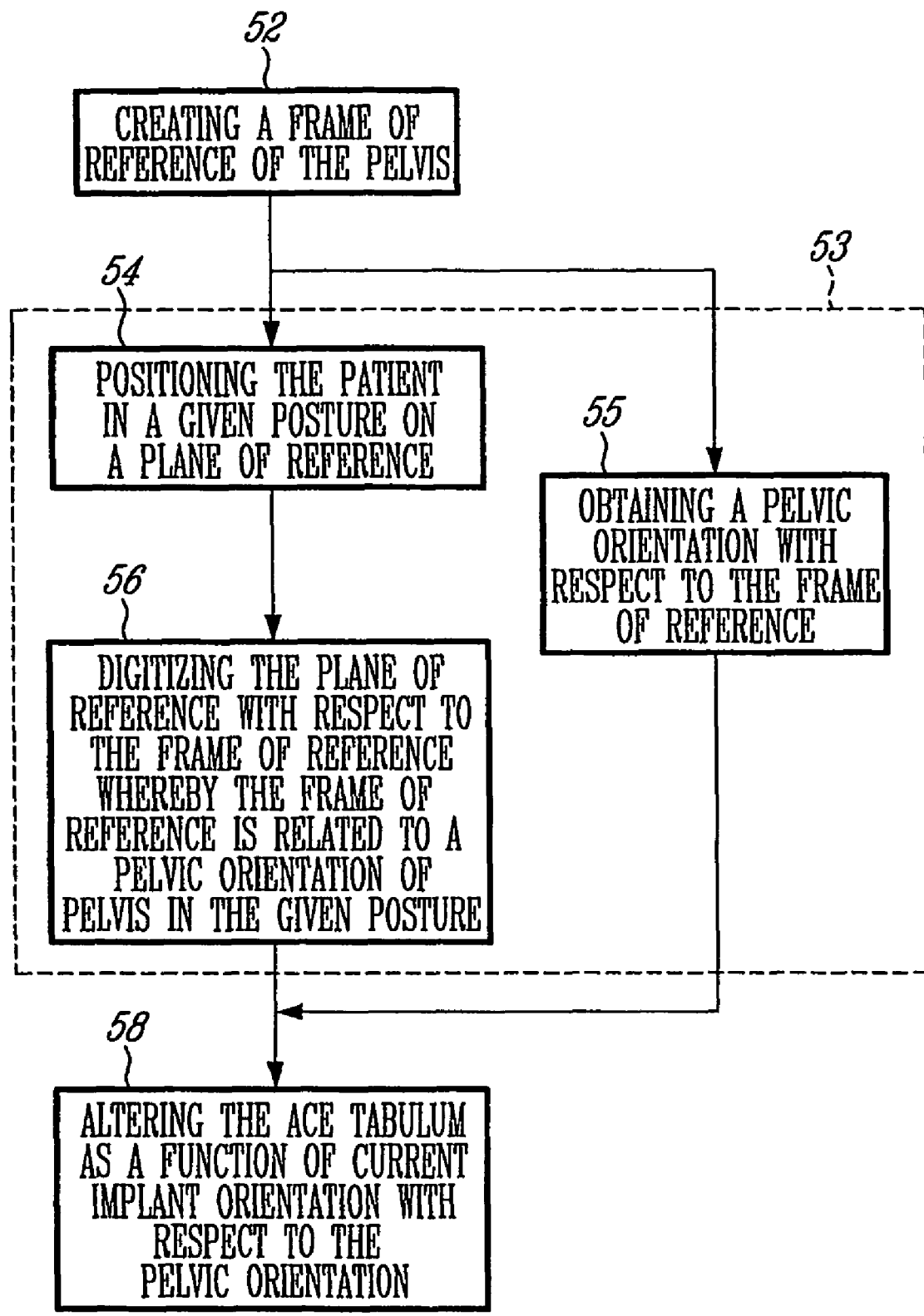
FIG_3

METHOD FOR PROVIDING PELVIC ORIENTATION INFORMATION IN COMPUTER-ASSISTED SURGERY

CROSS-REFERENCE TO RELATED APPLICATION

This application is a National Stage application of International patent application No. PCT/CA03/01542, filed on Oct. 6, 2003, which claims priority of U.S. Patent Application No. 60/415,809, filed on Oct. 4, 2002 by the present Applicants, the subject matter of which is incorporated herein by reference, and U.S. Patent Application No. 60/465,805, filed on Apr. 28, 2003 by the present Applicants, the subject matter of which is incorporated herein by reference.

BACKGROUND OF THE INVENTION

1. Field of the Invention

The present invention generally relates to hip-replacement surgery using a computer-assisted surgery (CAS) system and, more particularly, to a method for orienting an acetabular implant for a CAS system.

2. Background Art

In hip-replacement surgery, optimal orientation of the pelvic prosthesis implant (also known as "acetabular implant" and "acetabular cup") in the acetabulum reduces the risks of limb length discrepancy and dislocation due to implant impingement.

In order to guide the surgeon in setting the acetabular implant in an optimal position, a CAS system provides position and orientation information during the operative steps. The information may be provided in the form of values including anteversion and inclination.

The anteversion and inclination values are related to a frame of reference of a patient. A frame of reference is defined preoperatively or intraoperatively, and this frame of reference is used as a reference for the anteversion and inclination values.

Various methods have been described to define frames of reference, some of which include forming digital planes on a pelvis from points digitized at predetermined landmarks. In the latter case, a certain level of reproducibility is attained from patient to patient as the predetermined landmarks are present on every patient. This level of reproducibility allows anteversion and inclination values to be compared from patient to patient, and surgeons may set the acetabular implant orientation of a patient within ranges of orientation he/she is familiar with.

The frames of reference currently used in CAS do not take into account the pelvic orientation with respect to the natural postures. For instance, a patient may have an abnormal pelvic orientation when standing straight, when lying. The pelvic orientation or pelvic tilt will have a direct effect on the actual anteversion and inclination values of the patient once the patient takes these postures.

SUMMARY OF INVENTION

It is an aim of the present invention to provide a computer-assisted surgery system for guiding a surgeon in inserting a pelvic implant as a function of a patient posture.

It is a further aim of the present invention to provide a method for inserting a pelvic implant as a function of the patient posture.

It is a still further aim of the present invention to provide a method for associating the patient posture to a frame of reference of the pelvis.

It is a still further aim that the methods of the present invention provide precision and accuracy in orienting the pelvic implant.

Therefore, in accordance with the present invention, there is provided a computer-assisted surgery system for guiding an operator in altering a pelvis for a subsequent insertion of a pelvic implant, comprising: a sensing apparatus adapted to track a reference tool securable to the pelvis and a bone altering tool for position and orientation; a position calculator connected to the sensing apparatus for calculating a position and orientation of a pelvic frame of reference as a function of the position and orientation of the reference tool, and for calculating a position and orientation of the bone altering tool with respect to the frame of reference when altering the pelvis; a source of posture data; a posture data correction calculator operative to provide a display of information allowing an operator to take into consideration said posture data from the source of posture data when altering the pelvis; and a display unit connected to the position calculator and to the posture data correction calculator for displaying said display of information and the position and orientation of the bone altering tool with respect to the pelvic frame of reference.

Further in accordance with the present invention, there is provided a method for guiding an operator in altering a pelvis or a subsequent insertion of a pelvic implant in computer-assisted surgery, comprising the steps of: creating a frame of reference related to geometry information of a pelvis, the frame of reference being trackable for position and orientation; obtaining a pelvic orientation relating to a given posture of the patient with respect to the frame of reference; and altering the acetabulum for a subsequent insertion of the pelvic implant in the acetabulum by presenting information about a current implant orientation with respect to said pelvic orientation, the current implant orientation being calculated as a function of a tracking of a surgical tool altering the acetabulum for receiving the pelvic implant, and of the frame of reference.

Still further in accordance with the present invention, there is provided a method for associating a frame of reference of a pelvis to a given posture of a patient in computer-assisted surgery, comprising the steps of: creating a frame of reference of a pelvis by registering points on the pelvis with respect to a trackable reference; positioning the patient in a given posture with respect to a plane of reference; and digitizing the plane of reference with respect to the trackable reference such that orientation information associating the frame of reference to the given posture is calculable as a function of the orientation of the plane of reference.

Still further in accordance with the present invention, there is provided a computer-assisted surgery system for performing total hip replacement surgery, the system comprising at lest one tracked instrument, characterized in that said system further comprises a module taking input data relating to landmark/anatomical reference positions at points on a patient's body from said tracked instrument to calculate a pelvic orientation with respect to a patient posture.

BRIEF DESCRIPTION OF THE DRAWINGS

Having thus generally described the nature of the invention, reference will now be made to the accompanying drawings, showing by way of illustration a preferred embodiment thereof and in which:

FIG. 2 is a frontal view of a pelvis with landmarks used with the methods of the present invention; and FIG. 3 is a flowchart illustrating a method for associating the patient posture to a frame of reference of the pelvis in accordance with the present invention.

DESCRIPTION OF THE PREFERRED EMBODIMENTS

The Computer-Assisted Surgery System

Figure 1:
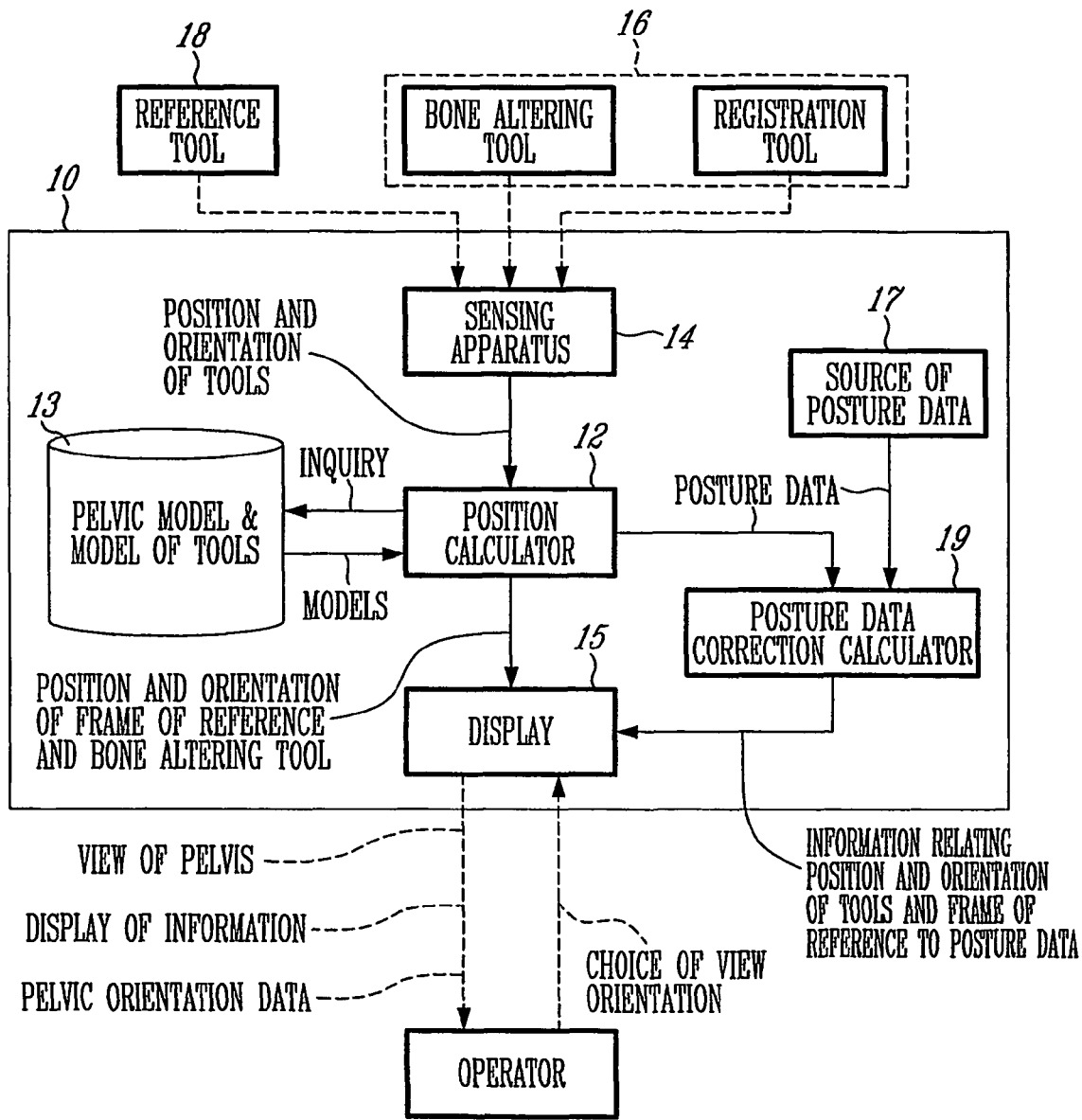
FIG. 1 is a block diagram of a computer-assisted surgery system for guiding an operator in inserting a pelvic implant in an acetabulum in accordance with an embodiment of the present invention.

The present invention operates with a typical computer-assisted surgery system. Accordingly, a computer-assisted surgery system is now described for reference purposes, and suitable variants thereof can be used to perform the method of the present invention.

Referring to FIG. 1, a computer-assisted surgery system is generally shown at 10 (hereinafter "CAS system 10"), and generally consists of a CAS position calculator 12 connected to sensor apparatus 14. The sensor apparatus 14 tracks trackable tools 16 actively or passively for position and orientation, such as a registration pointer, a reference tracker, a reamer or an impactor, whose respective geometries are digitally known, so as to be associated, for instance, to a digital model of an acetabular implant (i.e., a pelvic implant). The position calculator 12 is typically a PC unit, with a calculator device, that has a database 13 and user interfaces (e.g., display interface 15) by which a surgeon will receive or send information that will guide him/her during surgery. For instance, monitors, keyboard, mouse and foot pedals are a few of the user interfaces that can be provided with the position calculator 12.

The CAS system 10 also has a posture data correction calculator 19, that is connected to the position calculator 12 and will determine the pelvic orientation value (i.e. posture data) in order to inform the surgeon/operator of the posture of the patient.

The registration pointer of the tools 16 has a tip of known configuration such that a position of a point at the tip is calculable as a function of a position and orientation tracking of the registration pointer, using geometry information of the registration pointer. The registration pointer is thus used to register the position of points. A reference tracker 18 is secured to objects (e.g., a pelvis) that will be registered such that the points that are registered with the registration pointer have a trackable reference.

Reference Coridnate System (Frame of Reference)

In hip-replacement surgery involving a CAS system such as the one described as 10 above, a reference coordinate system is defined for the pelvis so as to guide the surgeon in the implanting of the acetabular cup. Various methods have been described to define the reference coordinate systems on the pelvis. For instance, U.S. Patent Application No. 60/415, 809, upon which the present application claims priority, describes a method of creating a pelvic frontal plane of a patient, by registering three reference points on predetermined parts of the pelvis, to render this method reproducible.

More specifically, referring to FIGS. 1 and 2, the method involves anchoring the reference tracker 18 to a pelvis 20. Thereafter, three points are registered on the pelvis 20 using the registration pointer 16. In a preferred embodiment of U.S. Patent Application No. 60/415,809, these three points are outermost points 22 and 24 of the anterior-superior iliac spines, and one outermost point 26 of either one of the pubic tubercles, with respect to the reference tracker 18. The CAS system 10 uses the points 22, 24 and 26 to define a frontal plane of the pelvis with respect to the reference tracker 18. The sagittal and transverse planes are then calculated as a function of the frontal plane and other landmarks registered on the patient.

A medio-lateral axis 28 is defined by the position calculator 12 as passing through the outermost points 22 and 24 of the anterior-superior iliac spines, or as parallel to a segment passing through the outermost points 22 and 24 of the anterior-superior iliac spines, as illustrated in FIG. 2. A longitudinal axis 30 is defined by the position calculator 12 as being perpendicular to the medio-lateral axis 28 while lying in the frontal plane.

Pelvic Orientation/Posture Data Correction

The present invention relates the reference coordinate system of the pelvis to a pelvic orientation of the patient, so as to provide the surgeon with pelvic orientation information during surgery.

In the present invention, the pelvic orientation (also referred to as posture data hereinafter) is defined as the orientation of the pelvis with respect to a universal reference. The universal reference is a reference that can be used for every patient, whereby the pelvic orientation will be comparable between patients.

Therefore, in the present invention, the pelvic orientation is quantified, whereby abnormal pelvic orientations will be a known factor in hip replacement surgery.

More specifically, in a preferred embodiment, the CAS system 10 of the present invention provides medio-lateral and anterior-posterior orientation values of the pelvis 20 with respect to a reference plane associated with the posture of the patient, such as the OR table. Referring concurrently to FIGS. 1 and 3, a method for associating the frame of reference of the pelvis to the posture of the patient is generally shown at 50.

In Step 52, a frame of reference of the pelvis 20 is created. In the preferred embodiment of the present invention, planes are created by registering points on the pelvis 20, as described above. It is alternatively contemplated to obtain CT scans of the pelvis 20 and create a digital model or a coordinate system therefrom to obtain a pelvic frame of reference.

In Step 54, the patient is positioned on a reference surface such that a posture of the patient is obtained, in which a predetermined pelvic orientation is exposed. In a preferred embodiment, the patient lies on an OR table 32 (FIG. 2), and the surface of the OR table 32 can be used to define the plane of reference associated with the patient posture and the pelvic orientation.

The use of the OR table 32 (FIG. 2) is advantageous in that its plane of reference supports the patient on his/her back, and thus simulates a frontal plane of the patient, this frontal plane being reproducible for each patient. Accordingly, inter-patient comparisons can be made relating to this frontal plane, i.e., the plane of reference of the OR table 32 (FIG. 2).

In Step 56, the plane of reference is digitized. The reference plane is defined by registering three nonlinear points on the surface of the OR table 32 (FIG. 2) as a function of the reference tracker 18, using, for instance, the registration pointer from amongst the tools 16. For instance, these three nonlinear points are illustrated as points 34, 36 and 38 in FIG. 2.

The above-described Steps 54 and 56 are associated in a global Step 56 related to a preferred embodiment of the present invention, in which a plane of reference is used to obtain pelvic orientation information.

Alternatively, the pelvic orientation can be used using markers, from amongst the tools 16, pre-operatively or intraoperatively on various patient landmarks (e.g., in addition to the pelvis, the legs, the back, the spine, etc . . . ). In Step 55, the pelvic orientation is obtained and related to the reference coordinate system).

Following the alternative routes of Step 53, the CAS system 10 will have the orientation information necessary to associate the pelvic orientation (through the plane of reference) to the frame of reference of the pelvis 20, as shown in Step 58. As an example, the posture data correction calculator 19 can calculate orientation values of the pelvis 20 with respect to the medio-lateral axis 28 and the longitudinal axis 30, as a function of the plane of reference (e.g., OR table 32 of FIG. 2).

The medio-lateral orientation value is defined by the posture data correction calculator 19 as the inclination of the pelvis 20 on the longitudinal axis 30, and is calculated as the angle between the medio-lateral axis 28 and the OR table 32, as digitized previously. More specifically, the normal to the OR table 32 is projected onto the transverse plane of the reference coordinate system of the pelvis, and the angle between this projection and, for instance, the medio-lateral axis 28 or an intersection of the sagittal plane and the transverse plane of the reference coordinate system of the pelvis, will be the inclination value. A dynamic label (e.g., lateral right/lateral left) will identify the orientation values.

The anterior-posterior orientation value is defined by the posture data correction calculator 19 as the inclination of the pelvis 20 on the medio-lateral axis 28, and is calculated as the angle between the longitudinal axis 30 and the OR table 32, as digitized previously. This angle can be calculated by projecting the normal to the OR table 32 (i.e., the reference plane) on the sagittal plane, and measuring, for instance, the angle between the projection and the intersection of the transverse and sagittal planes of the reference coordinate systems of the pelvis. A dynamic label (e.g., anterior/posterior) will identify the orientation value.

These orientation values relating the patient posture to the frame of reference are usable in a number of ways in accordance with the present invention.

More specifically, the pelvic orientation information can be used by the CAS system 10 (through display 15) to guide the surgeon in inserting the acetabular implant. When a bone altering tool (such as a reamer) from amongst the tools 16 is tracked with respect to the reference tracker 18 to provide the current implant position and orientation in real time, the pelvic orientation values can be used to provide a relation between the current implant orientation and the patient posture.

For instance, orientation information about a reamer is displayed to the surgeon by the CAS system 10 in the form of anteversion and inclination values. In a preferred embodiment of the present invention, relating to U.S. Patent Application No. 60/415,809, the anteversion is the angle between an intersection of the pelvic frontal plane and the pelvic transverse plane, and a projection of a longitudinal axis of the reamer on the transverse plane. The inclination is the angle between the reamer axis and the cranial-caudal axis on the pelvic sagittal plane. The anterior-posterior orientation value can be used in the calculation of the anteversion and of the inclination, such that the anteversion and the inclination are related to the pelvic orientation, and hence to the patient posture.

For example, the anterior-posterior orientation value will be used to bring the anteversion to the plane of reference. This is performed in a preferred embodiment of the present invention by relating the anterior-posterior orientation value of the pelvis to the anteversion such that the anteversion is as a function of the patient posture rather than as a function of the reference coordinate system of the pelvis. For this calculation, a second reference coordinate system is created, in which the reference plane (e.g., the OR table 32) is the frontal plane. In other words, the frontal plane of the second reference coordinate system is the frontal plane of the initial reference coordinate system rotated about the medio-lateral axis 28 by the anterior-posterior orientation value. This second reference coordinate system may have its frontal plane rotated about the longitudinal axis 30 by the medio-lateral orientation value, starting from the frontal plane of the initial reference coordinate system. In the case of the inclination, the cranial-caudal axis will be adjusted from the pelvic frontal plane to the plane of reference using the anterior-posterior orientation value.

Therefore, in the surgical steps of the alteration of the acetabulum, the current implant orientation, provided through anteversion and inclination values of the bone altering tools, will take into account the posture of the patient, and hence the pelvic orientation. Advantageously, patient-to-patient comparisons will be possible when taking into account the pelvic orientation of the patient.

Alternatively, the anterior-posterior and the medio-lateral orientation values can be used to visually adjust the anterior-posterior and medio-lateral views of the pelvis through the display interface 15 of the CAS system 10. In these views, the graphic representation of the pelvis could be oriented to represent the pelvic orientation at the given posture, serving as a visual aid in guiding the system, and is illustrated broadly by source of posture data 17 in FIG. 1.

The orientation values can also be used, for instance, by the surgeon as a patient-to-patient comparison basis for typical frontal plane inclination. The orientation values may also be used as a comparison basis with the CT scan of the pelvis 20, usually taken preoperatively. The CT scan is taken with the patient lying on the CT-scan table, and thus the orientation values that will be described hereinbelow can be compared to the CT scan as the patient lies on the OR table 32 when the orientation values are calculated.

The above-described method measures the orientation values of the pelvis 20 with respect to the reference tracker 18 that is fixed to the pelvis 20. Therefore, the orientation values are temporary, as they are fixed in time at the moment the OR table 32 is digitized. It is, therefore, contemplated to provide a reference tracker 34 on the OR table 32, with the three points digitized on the OR table 32 being registered as a function of the reference tracker 34 rather than the reference tracker 18. This provides the advantage of giving real-time orientation values, rather than a picture of the orientation values.

It is contemplated to compute the reference coordinate system of the patient using other methods to obtain the medio-lateral axis 28 and the longitudinal axis 30. The orientation values measured thereafter using the method of the present invention will be relative to the method used to define the reference coordinate system of the patient. Alternatively, the pelvic orientation information can be obtained using other methods. For instance, a pelvic frame of reference can be digitized as a function of other bodily elements of the patient providing some information about the orientation of this pelvic frame of reference. Also, noninvasive markers can be positioned onto the skin in the pelvis area, and pelvic orientation information can be obtained from a standing posture of the patient, with these steps being performed preoperatively. Such a method is described in U.S. Pat. No. 6,514,219, issued on Feb. 4, 2003, to Guimond et al.

We claim:

1. A computer-assisted surgery system for guiding an operator in altering a pelvis for a subsequent insertion of a pelvic implant, comprising:
   a sensing apparatus configured to track a reference tool securable to the pelvis and a bone altering tool at least in orientation;
   a position calculator for calculating at least an orientation of a pelvic frame of reference as a function of a tracking of the reference tool, and for calculating at least an orientation of the bone altering tool with respect to the frame of reference when altering the pelvis;
   a source of posture data being a tool digitizing a plane related to a given posture of the patient;
   a posture data correction calculator operative to provide a display of information comprising the frame of reference corrected based on said posture data from the source of posture data when altering the pelvis; and
   a display unit for displaying said display of information and the orientation of the bone altering tool with respect to the pelvic frame of reference.

2. The computer-assisted surgery system according to claim 1, wherein said display of information is a corrected view of the frame of reference with respect to said posture data on the display unit.

3. The computer-assisted surgery system according to claim 1, wherein said display of information is additional information relating the frame of reference to said posture data.

4. The computer-assisted surgery system according to claim 3, wherein said additional information includes an anteversion value and an inclination value of the bone altering tool related to said posture data.

5. The computer-assisted surgery system according to claim 1, wherein the tool is a registration tool trackable by the sensing apparatus, the registration tool being used with the position calculator to digitize a plane supporting the patient in the given posture with respect to the frame of reference, said posture data being associated with an orientation of said plane.

6. A method for guiding an operator in altering a pelvis for a subsequent insertion of a pelvic implant in computer-assisted surgery, comprising:
   creating a frame of reference related to geometry information of a pelvis, the frame of reference being trackable at least in orientation;
   obtaining a pelvic orientation relating to a given posture of the patient with respect to the frame of reference;
   correcting the pelvic orientation as a function of an orientation of a plane supporting the patient in the given posture; and
   altering the acetabulum for a subsequent insertion of the pelvic implant in the acetabulum by presenting information about a current implant orientation with respect to said corrected pelvic orientation, the current implant orientation being calculated as a function of a tracking of a surgical tool altering the acetabulum for receiving the pelvic implant, and of the frame of reference.

7. The method according to claim 6, wherein the current implant orientation comprises at least one of an anteversion value and an inclination value related to the orientation of the plane.

8. The method according to claim 6, wherein the current implant orientation is at least one of an anteversion value and an inclination value related to said corrected pelvic orientation.

9. The method according to claim 8, wherein any one of the anteversion value and the inclination value is related to said corrected pelvic orientation by a display interface displaying a pelvis image oriented to said pelvic orientation in combination with an axis of any one of the anteversion value and the inclination value.

10. The method according to claim 8, wherein any one of the anteversion value and the inclination value is calculated taking into account the orientation of the plane of reference with respect to the frame of reference.

11. The method according to claim 6, wherein the current implant orientation is related to said corrected pelvic orientation by a display interface displaying a pelvis image oriented to said corrected pelvic orientation in combination with the current implant orientation.

12. The method according to claim 6, wherein the method is performed on an anatomical bone model or on a cadaver.

13. A method for associating a frame of reference of a pelvis to a given posture of a patient in computer-assisted surgery, comprising:
   creating a frame of reference of a pelvis with respect to a trackable reference; positioning the patient in a given posture with respect to a plane of reference;
   digitizing the plane of reference with respect to the trackable reference such that orientation information associating the frame of reference to the given posture is calculable as a function of the orientation of the plane of reference; and
   obtaining a display of information comprising the frame of reference corrected based on said orientation information.

14. The method according to claim 13, wherein the frame of reference comprises a frontal plane defined with outermost points of the anterior-superior iliac spines and an outermost point of any one of the pubic tubercles.

15. The method according to claim 14, wherein the given posture has a medio-lateral value defined by an angle between an axis lying in the frontal plane and being parallel to a segment passing through the outermost points of the anterior-superior iliac spines, and the plane of reference.

16. The method according to claim 14, wherein the given posture has an anterior-posterior value defined by an angle between an axis lying in the frontal plane and being perpendicular to a segment passing through the outermost points of the anterior-superior iliac spines, and the plane of reference.

17. The method according to claim 14, wherein the given posture has the back of the patient lying on the plane of reference.

18. The method according to claim 13, wherein the method is performed on an anatomical bone model or on a cadaver.

* * * * *